(12) United States Patent
Fitzgerald et al.

(10) Patent No.: US 7,612,341 B2
(45) Date of Patent: Nov. 3, 2009

(54) IMAGE OF SAMPLE USING TERAHERTZ TIME DOMAIN SPECTROSCOPY IN REFLECTION MODE TO IDENTIFY IN A FIRST MATERIAL LIKE NORMAL BREAST TISSUE A SECOND MATERIAL LIKE CANCEROUS TISSUE BY EVALUATING THE PHASE CHANGE AT THE INTERFACE BETWEEN THE SAMPLE AND A WINDOW LIKE A QUARTZ WINDOW, AGAINST WHICH THE SAMPLE IS PRESSED

(75) Inventors: Anthony J. Fitzgerald, Cambridgeshire (GB); Vincent P. Wallace, Cambridgeshire (GB)

(73) Assignee: TeraView Limited, Cambridge (GB)

( * ) Notice: Subject to any disclaimer, the term of this patent is extended or adjusted under 35 U.S.C. 154(b) by 0 days.

(21) Appl. No.: 11/631,092

(22) PCT Filed: Jun. 28, 2005

(86) PCT No.: PCT/GB2005/002585

§ 371 (c)(1),
(2), (4) Date: Mar. 1, 2007

(87) PCT Pub. No.: WO2006/000831

PCT Pub. Date: Jan. 5, 2006

(65) Prior Publication Data

US 2007/0296957 A1 Dec. 27, 2007

(30) Foreign Application Priority Data

Jun. 29, 2004 (GB) .................................. 0414554.6

(51) Int. Cl.
*G01J 5/02* (2006.01)

(52) U.S. Cl. .................................................. 250/341.1

(58) Field of Classification Search ............... 250/341.1
See application file for complete search history.

(56) References Cited

U.S. PATENT DOCUMENTS

| | | | | |
|---|---|---|---|---|
| 5,293,213 | A | * | 3/1994 | Klein et al. .................. 356/484 |
| 7,174,037 | B2 | * | 2/2007 | Arnone et al. ............... 382/128 |
| 2003/0178584 | A1 | * | 9/2003 | Arnone et al. ........... 250/495.1 |

FOREIGN PATENT DOCUMENTS

| | | |
|---|---|---|
| GB | 2 347 835 | 9/2000 |
| GB | 2 380 920 | 4/2003 |
| WO | WO 00/50859 | 8/2000 |

OTHER PUBLICATIONS

Cole et al. (2001) Terahertz Imaging and Spectroscopy of Human Skin, In-vivo, Proceedings of SPIE vol. 4276, pp. 1-10.*

(Continued)

*Primary Examiner*—David P Porta
*Assistant Examiner*—Marcus H Taningco
(74) *Attorney, Agent, or Firm*—Dickstein Shapiro LLP

(57) ABSTRACT

A method of investigating a sample (breast tissue) (27), the sample comprising at least a first material (normal breast tissue) in order to determine they presence of at least one further material (cancerous tissue), the method comprising the steps of: Irradiating the sample with electromagnetic radiation in the range from 25 GHz to 100 THz; Detecting radiation reflected from the sample; Determining a parameter related to the amplitude of the radiation, which is reflected from the sample, in the time domain; Analyzing the parameter derived in step (c) in order to determine if the sample further comprises the at least one further material wherein the irradiating and reflected radiation passes through a (z-cut quartz) window member (43) having a refractive index that falls between the refractive indices of the at least first and at least one further materials.

11 Claims, 10 Drawing Sheets

OTHER PUBLICATIONS

Woodward, R. M. et al., "Tissue Classification Using Terahertz Pulsed Imaging" The Institution of Electrical Engineers, Stevenage, GB; 2004, Abstract.

Woodward, R. M. et al., "Tissue Classification Using Terahertz Pulsed Imaging" Proceedings of the SPIE—The International Society for Optical Engineering SPIE-Int. Soc. Opt. Eng. USA, vol. 5318, No. 1, 2004, pp. 23-33. Advanced Biomedical and Clinical Diagnostic Systems II 25-26, Jan. 2004, San Jose, CA, USA, vol. 5318, No. 1, pp. 23-33, Jan. 25-26, 2004, Proceedings of the SPIE—The International Society for Optical Engineering SPIE—Int. Soc. Opt. Eng USA.

Wallace, V.P., "Biomedical Applications of THz Imaging" Microwave Symposium Digest, 2004, IEEE MTT-S International Fort Worth, TX, USA, Jun. 6-11, 2004, Piscataway, NJ, USA, IEEE, vol. 3, Jun. 6, 2004, pp. 1579-1581.

Wallace, V. P., :Biomedical Applications of Terahertz Pulse Imaging Second Joint EMBS-BMES Conference 2002. Conference Proceedings. 24th Annual International Conference of the Engineering in Medicinel and Biology Society. Annual Fall Meeting of the Biomedical Engineering Society, Houston, TX, Oct. 23-26, 2002, Annua, vol. vol. 1 of 3. Conf. 24, Oct. 23, 2002, pp. 2333-2334.

Fitzgerald, A. J. et al., "Terahertz Imaging of Breast Cancer, a Feasibility Study" Conference Digest of the 2004 Joint 29th International Conference on Infrared and Millimeter Waves and 12th International Conference on Terahertz Electronics IEEE Piscataway, NJ, USA, 2004, pp. 823-824.

* cited by examiner

IMAGE OF SAMPLE USING TERAHERTZ TIME DOMAIN SPECTROSCOPY IN REFLECTION MODE TO IDENTIFY IN A FIRST MATERIAL LIKE NORMAL BREAST TISSUE A SECOND MATERIAL LIKE CANCEROUS TISSUE BY EVALUATING THE PHASE CHANGE AT THE INTERFACE BETWEEN THE SAMPLE AND A WINDOW LIKE A QUARTZ WINDOW, AGAINST WHICH THE SAMPLE IS PRESSED

The present invention relates to the field of imaging samples with radiation in the infra-red (IR) and Terahertz frequency range and specifically using radiation in the higher Gigahertz (GHz) and the Terahertz (THz) frequency ranges. In this field, all such radiation is colloquially referred to as THz radiation, particularly that in the range from 25 GHz to 100 THz, more particularly that in the range of 50 GHz to 84 THz, especially that in the range from 100 GHz to 50 THz.

Such radiation is non-ionising and, as a result, it is particularly of use in medical applications. In medical imaging, the radiation is generally reflected from the patient.

Components of the sample being imaged will have a frequency dependent absorption coefficient and refractive index, thus each component of a sample subjected to radiation will leave its own characteristic fingerprint in the detected radiation. Thus, researchers have attempted to image samples using a plurality of frequencies to create an image from spectral information.

Measurements have been made using both frequency domain techniques, (where the amplitude of each frequency components is analysed), and time domain techniques, (where the radiation is analysed as a function of the delay time introduced by the sample into the path of the radiation). Time domain imaging is described in earlier patent GB 2 347 835.

For imaging, in the time domain, a time domain waveform is obtained for each pixel of the sample. It is then necessary to obtain a single parameter from each waveform to plot for each pixel. Previous attempts at producing images from such waveforms have used the amplitude of the highest maximum or lowest minimum.

It is an object of the present invention to provide a method and apparatus which derives a parameter from time domain spectra to allow an image with enhanced contrast to be generated. The image can be a two dimensional image of an area of a sample, or it may be a profile of a line passing through the sample.

It is a further object of the present invention to provide a method of investigating a sample in order to determine the presence of a material.

Accordingly, in a first aspect of the invention, there is provided a method of investigating a sample, the sample comprising at least a first material in order to determine the presence of at least one further material, the method comprising the steps of: a) Irradiating the sample with electromagnetic radiation in the range from 25 GHz to 100 THz; (b) Detecting radiation reflected from sample; (c) Determining a parameter related to the amplitude of the radiation, which is reflected from the sample, in the time domain; and (d) Analysing the parameter derived in step (c) in order to determine if the sample further comprises the at least one further material wherein the irradiating and reflected radiation passes through a window member having a refractive index that falls between the refractive indices of the at least first and at least one further materials.

In a second aspect of the present invention there is provided a method of imaging a sample the sample comprising at least a first material and at least one further material, the method comprising the steps of: (a) Irradiating the sample with electromagnetic radiation in the range from 25 GHz to 100 THz; (b) Detecting radiation reflected from sample; (c) Determining a parameter related to the amplitude of the radiation, which is reflected from the sample, in the time domain; (d) generating an image by plotting the value of the parameter calculated in step (c) for different points of the sample wherein the irradiating and reflected radiation passes through a window member having a refractive index that falls between the refractive indices of the at least a first and at least one further materials.

Whenever an electromagnetic wave travelling through a medium approaches a boundary with another medium where the wave velocity is different a portion of the wave will be reflected. Depending on the characteristics of the media either side of the boundary the wave may be reflected with an associated change of phase. For example, where the refractive index of the medium after the boundary is higher than the refractive index of the medium before the boundary the wave will be reflected with an associated 180 degree change in phase. However, if the refractive index drops across the boundary then the reflected wave will not change in phase (see also FIG. 2).

The present invention exploits phase change effects at a boundary in order to provide an improved method of investigating and imaging a sample. In the present invention radiation irradiating a sample and radiation reflected from the sample passes through a window member (which would usually be in contact with the sample to maximise the efficiency of the system set-up). The window member is chosen such that it has a refractive index that is greater than some materials within the sample and less than other materials within the sample. In this manner, the detected radiation will either exhibit no phase change or a 180 degree phase change (relative to the irradiating radiation) depending on the components of the sample under investigation. Therefore the method according to the first aspect of the present invention allows a simple determination of the presence of at least one material within the sample under investigation by analysing a predetermined parameter of the detected radiation in order to ascertain whether there is any change in phase of the radiation compared to the irradiating radiation. The method of the present invention provides a simple and rapid method by which the presence of a material can be detected. Furthermore, it can be used with systems that operate with a low signal to noise ratio which may be the case for very rapid data acquisition.

For example, for a sample comprising a component having a refractive index of 1.5 and further potentially comprising a component having a refractive index of 2.5 the window member may conveniently be chosen to have a refractive index, n, of, for example, n=2.

Radiation reflecting from regions of the sample where the refractive index is 1.5 will exhibit no phase change (since the refractive index drops across the window-sample boundary). By contrast, radiation reflecting (or transmitting) from regions of the sample where the refractive index is 2.5 will exhibit a phase change of 180 degrees (since the refractive index increases across the window-sample boundary).

Therefore by analysing the phase of a predetermined parameter of the detected radiation the presence (or absence) of the second material may be determined.

The parameter of the detected radiation can conveniently either be directly analysed (as per the first aspect of the invention) or alternatively can be used to plot an image of the sample.

The parameter that is measured may conveniently be related to a maxima or minima in the detected radiation. Alternatively, the parameter may represent a ratio of measured radiation values at two separate time intervals.

The parameter may be the amplitude of the radiation itself. However, preferably, the detected amplitude is processed in order to obtain a parameter.

When imaging non-rigid samples, it is preferable if a flat surface is provided for receiving the radiation. This is provided by the window which is transparent to the irradiating radiation. The sample is pressed against this window to provide a flat analysis surface. However, the window itself can cause its own problems. This is because the window, has two interfaces, a front interface upon which the irradiating radiation is directly incident and a back surface which abuts the sample. Both of these surfaces will reflect radiation giving rise to at least two unwanted signals in the detected reflected radiation. We refer to at least two reflections because multiple internal reflections may occur within the window giving even further unwanted effects.

Preferably, steps are taken in order to remove this so-called "baseline" signal. Thus, if step (a) comprises a step of irradiating the sample through the member which is transparent to the irradiating radiation and which abuts the sample, the method preferably further comprises the step of obtaining a baseline signal by irradiating the member in the absence of the sample and detecting the amplitude of the reflected radiation. The parameter is then determined by subtracting the baseline signal from the detected amplitude of the reflected radiation from both the member and the sample.

The baseline signal can be subtracted from the amplitude of the detected reflected radiation in the time domain or the frequency domain. The frequency domain signal is created by Fourier transforming the time domain signal.

In addition to or as an alternative, it may also be desirable to obtain a reference signal which is obtained by replacing the sample with the reference object of known reflectance and measuring the amplitude of radiation reflected from the reference object. The parameter is then derived by dividing the detected amplitude of the radiation from the sample with the reference signal in the frequency domain.

Where both a reference signal and a baseline signal are obtained, the baseline signal is subtracted from both the sample signal and the reference signal and the baseline subtracted sample signal is then divided by the baseline subtracted reference signal. This division is performed in the frequency domain.

A sample signal which has been baseline subtracted, divided by a reference signal and filtered is referred to as the impulse function. Preferably, the parameter is derived from the impulse function.

Suitable materials for use as the window member should be transparent to THz radiation and include high resistivity silicon, z-cut quartz, TPX, polystyrene or polyethene.

Preferably the refractive index of the window member is substantially constant with frequency within the THz region.

The inventors have discovered that the above aspects of the present invention are particularly suited to the investigation and imaging of cancerous tissue. It has further been noted that the use of quartz as a window member is particularly advantageous in the imaging of cancerous skin and breast tissue. This is because the refractive index of quartz is closely matched to the refractive index of skin thereby reducing the amount of reflection from the surface of the sample and giving greater sensitivity to depth information. Furthermore, for breast tissue it is noted that the refractive index of normal breast tissue and cancerous tissue fall either side of the refractive index of quartz. Therefore, quartz is a particularly advantageous choice of material for use as a window member for identifying tumours.

Therefore the third aspect of the present invention provides for the use of quartz in a THz medical scanning apparatus wherein the apparatus comprises a source for irradiating a sample with a pulse of electromagnetic radiation, said pulse having a plurality of frequencies in the range 25 GHz to 100 Thz; detector means for detecting the amplitude of radiation reflected from the sample and a quartz window member wherein the irradiating and reflected/transmitted radiation passes through the quartz window member.

A fourth aspect of the present invention provides an apparatus for imaging a sample according to the method of the second and third aspects of the present invention, the apparatus comprising a source for irradiating a sample with a pulse of electro-magnetic radiation, said pulse having a plurality of frequencies in the range 25 GHz to 100 Thz; detector means for detecting the amplitude of radiation reflected from the sample; calculating means for determining a parameter related to the amplitude of the radiation, which is reflected from the sample, in the time domain; imaging means for generating an image by plotting the value calculated by the calculating means for different points of the sample wherein the apparatus further comprises a window member through which the irradiating and reflected radiation passes, the window member arranged to have a refractive index that falls between the refractive indices of the at least a first and at least one further material of the sample to be imaged.

Embodiments of the invention will now be described, by way of example only, with reference to the following Figures in which FIG. 1 shows a schematic of a reflection imaging system which may be used in accordance with an embodiment of the present invention FIG. 2 illustrates the effect of refractive index changes on THz pulses reflected from a boundary FIG. 3 shows a window member in accordance with the present invention FIGS. 4*a* and 4*b* show time domain waveforms measured when using the window member of FIG. 3.

FIGS. 5*a* and 5*b* show the time domain waveforms of FIGS. 4*a* and 4*b* following the subtraction of a baseline and deconvolution of a reference signal FIGS. 6*a* to 6*h* show images of the window member of FIG. 3 for various window materials and measurement parameters following the subtraction of a baseline and deconvolution of a reference signal.

FIG. 7 illustrates a plurality of deconvoled impulse functions for a sample of a skin tumour FIG. 8 shows impulse functions for normal and cancerous breast tissue when imaged using a THz method according to the present invention FIG. 9 is a photograph of histology for a breast tumour FIG. 10*a* is an image of the tumour of FIG. 9 generated using E(min)

FIG. 10*b* is an image of the tumour of FIG. 9 generated using the ratio E(max) to E(min)

FIG. 1 shows a TeraHertz scanning arrangement according to the prior art in which a sample of a solid or semi-solid composition undergoes Terahertz spectroscopy.

The apparatus comprises an ultra-short pulse laser 1 which may be, for example, Ti:sapphire, Yb:Er doped fibre, Cr:L-iSAF, Yb:silica, Nd:YLF, Nd:Glass, Nd:YAG or Alexandrite laser. This laser 1 emits pulses of radiation 3, such as a collimated beam of pulses, each of which comprise a plurality of frequencies. This pulse is reflected by first mirror 5 into beam splitter 7. The beam splitter splits the beam into a pump pulse 9 which is used to irradiate the sample and a probe pulse 11 which is used during detection.

The probe pulse 11 is directed into a scanning delay line 13, which adjusts the relative path-lengths between the pump and probe beams.

The pump pulse 9 is directed by mirrors 15 into lens 17, which is preferably an aspherical glass lens, when used for NIR. Lens 17 focuses the pump pulse onto a source 19 which preferably comprises a frequency conversion member and a bow-tie emitter. The frequency conversion member is configured to mix the incident radiation in order to output radiation derived from the differences of the input frequencies, so-called difference frequency generation. This technique is described in more detail in GB 2 347 835.

The emitter 19 abuts a hyper-hemispherical lens 21. The terahertz beam that is output from the emitter 19 is directed by the first silicon hyper-hemispherical lens 21 towards a first parabolic mirror 23. The beam is then reflected off the first parabolic mirror 23 and onto second parabolic mirror 25, which directs the radiation onto sample 27. The sample may be replaced with a reference sample in order to remove background features from the final results. The radiation which is reflected from sample 27 is then collected by third parabolic mirror 29 and onto a fourth parabolic mirror 31 which directs the reflected radiation onto a second hyper-hemispherical lens 33 and onto a detector 35, such as a photoconductive detector. The pump beam 9 as reflected off the sample is re-combined with the probe pulse 11 at the receiver 35.

Prior to recombining with the pump beam 9, the probe beam 11 is directed into second scanning delay line 13. This delay line is a rapid-scanning type and in its simplest form comprises two mirrors that serve to reflect the beam through a 180° angle. These mirrors are then quickly swept backwards and forwards in order to vary the path length of the pump pulse 11.

The probe beam 11 output from the scanning delay line 13 is then reflected off first probe beam mirror 37 onto second probe beam mirror 39 which directs the probe beam through lens 41, which is an aspherical glass lens when used to focus NIR beams. This lens 41 focuses the probe beam onto the receiver 35 for combining with the reflected pump beam.

The sample introduces a time delay in the path of the pump pulse. The delay is dependent on both the absorption coefficient and the refractive index of the sample. In order to obtain a detection signal, the frequency component of the probe beam must be in phase with a frequency component of the pump beam. Variation of the scanning delay line allows the phase of the probe beam to be swept with respect to the pump beam and thus allows for measurement of the delay time of each frequency component which passes through the sample.

When imaging non-rigid samples, it is preferable if a flat surface is provided for receiving the radiation. This is provided by a window member 43 which is transparent to the irradiating radiation. The sample is pressed against this window to provide a flat analysis surface. When used in medical applications, the window member 43 will be in contact with an area of tissue to be imaged. The window member is therefore often referred to as the "contact material" or the "tissue contact material". It should be noted however that the three terms are interchangeable and identical.

FIGS. 2a and 2b show how the phase of an electromagnetic wave is affected as it crosses a boundary between two regions of differing refractive index. In FIG. 2a the wave travels from a medium with refractive index $n_a$ into a region with a higher refractive index $n_b (>n_a)$. The reflected wave in this case undergoes a phase change of 180°. By contrast, in FIG. 2b, where $n_a > n_b$ (i.e. wave travels into a lower refractive index) there is no change in the phase of the wave.

The invention exploits the phase change boundary physics described with reference to FIGS. 2a and 2b in order to distinguish between samples containing materials of differing refractive indices.

FIGS. 3-7 show how materials of different refractive indexes can be distinguished. In FIG. 3 a window member 45 is coated with three different materials, water 47, galden 49 and Isopropyl alcohol (IPA) 51. The three materials (47, 49, 51) have differing refractive indexes—for water, n=2.2; for IPA, n~1.6 and for galden, n=1.4. The three materials are also all clear, colourless fluids.

The coated window member of FIG. 3 was placed into a THz apparatus similar to that shown in FIG. 1 and the water/galden/IPA sample was then irradiated with THz radiation using firstly quartz (n=2.1) as the window member and secondly using polythene (n~1.5) as the window member.

FIG. 4a shows the raw waveforms recorded from the set up of FIG. 3 when the window member was polythene. FIG. 4b shows the raw waveforms recorded from the set up of FIG. 3 when the window member was quartz. In both FIGS. 4a and 4b water is designated by the black line, IPA by the grey line and galden by the dotted line.

The raw THz pulses recorded in FIGS. 4a and 4b were then converted to an impulse function by subtracting a baseline signal and deconvolving, in the frequency domain, a reference THz pulse reflected from the window-air interface without a sample present. The processed waveforms are shown in FIGS. 5a and 5b (Note: as before water is designated by the black line, IPA by the grey line and galden by the dotted line). GB 0201614.5 discloses a baseline subtraction method and is incorporated by reference.

It can be seen that the choice of the window member allows different materials to be distinguished. For example, in FIG. 5a, the window member (polythene) has a refractive index of 1.5. Since IPA and water have a higher refractive index than the window member the signal undergoes a phase change as described in FIG. 2 and therefore the waveforms relating to these two materials show a minimum value. In contrast the signal relating to galden (which has a lower refractive index than the window member) does not show a phase change. Therefore the presence of galden can be inferred by analysing the minimum value of the waveform, i.e. the "minimum of the impulse function" is the parameter that is "related to the amplitude of the detected radiation" that is determined in the method according to the first and second aspects of the present invention.

In FIG. 5b, the window member is quartz. Out of the three liquids on the window only water has a higher refractive index. Therefore only the water trace exhibits a phase change.

FIGS. 6a to 6h are equivalent to FIGS. 5a and 5b but show processed images (i.e. images of the area following the subtraction of a baseline signal as described above) of the window member instead of waveform traces. FIG. 6a depicts an image relating to the maximum of the detected impulse function where the window is polythene. FIG. 6b shows the same image as in FIG. 6a but with a quartz window.

Figure 1:
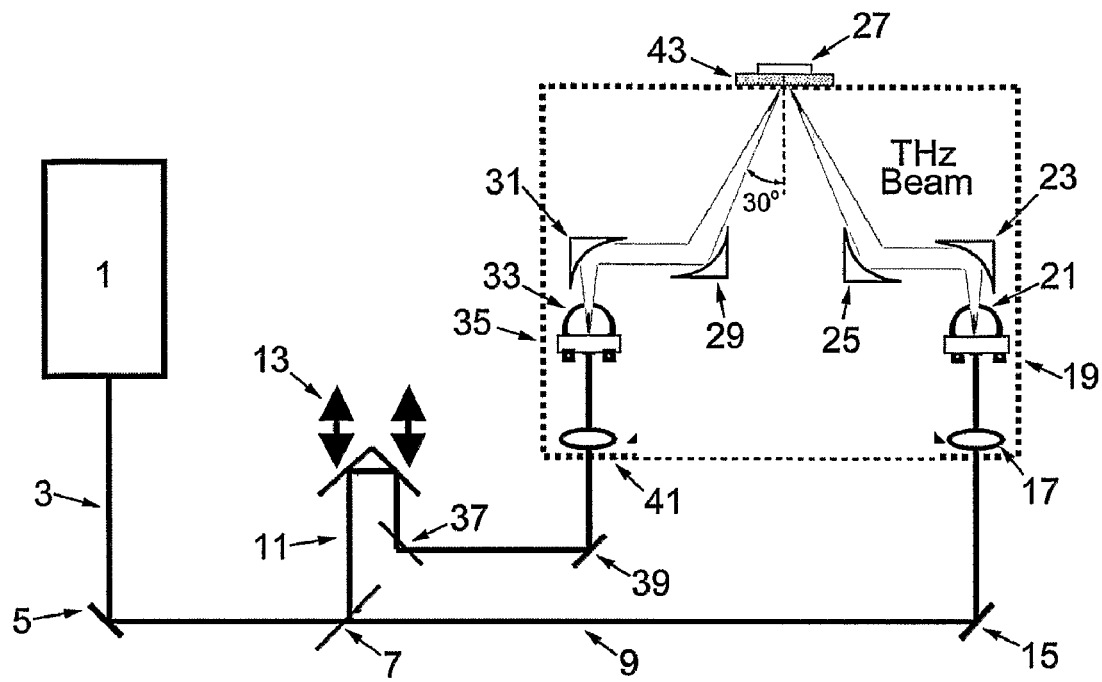
Figure 2A:
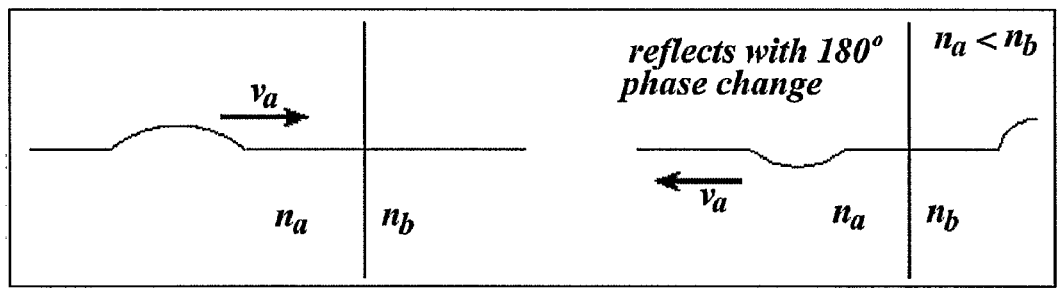
Figure 2B:
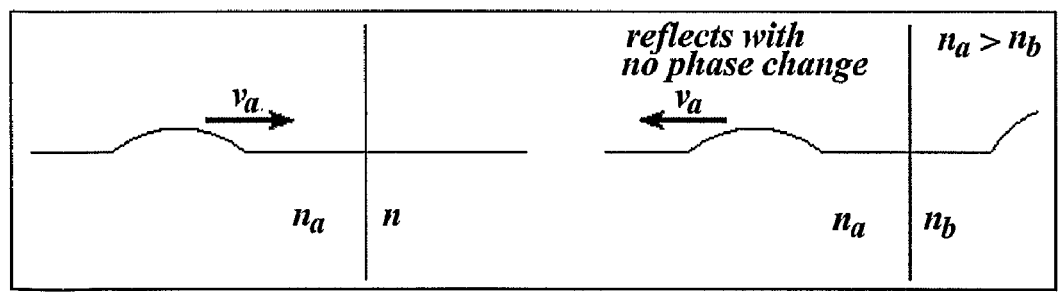
Figure 3:
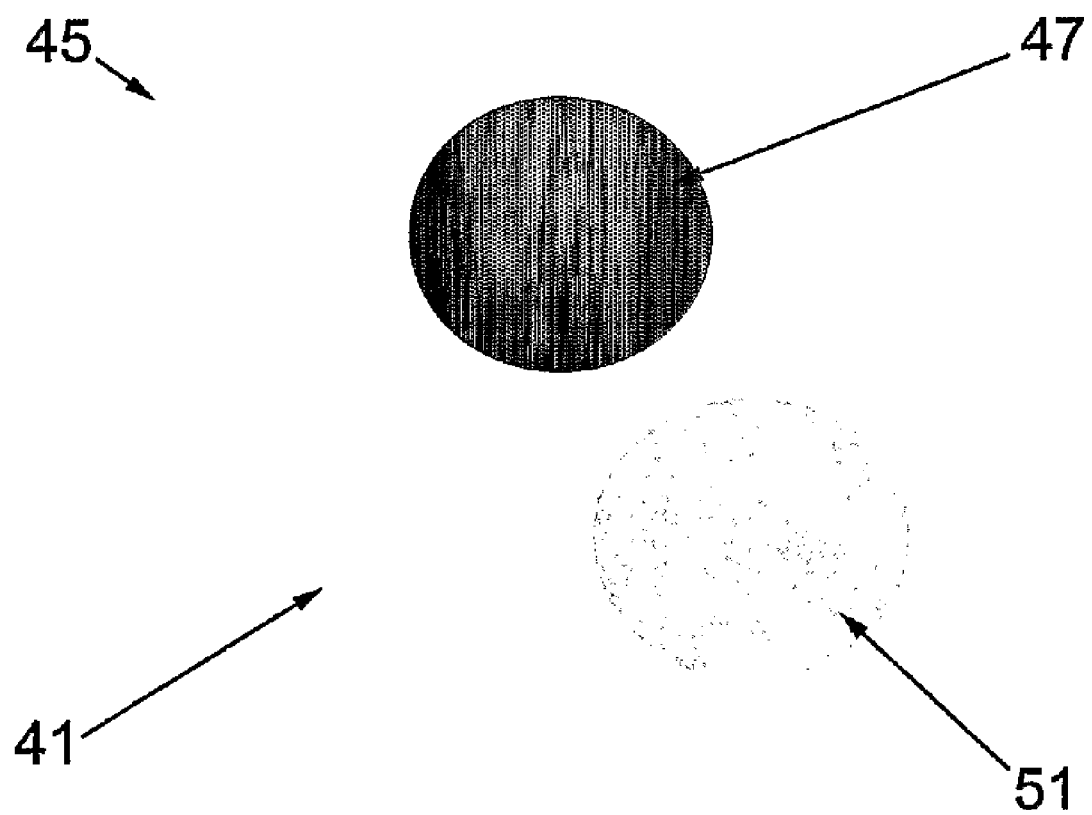
Figure 4A:
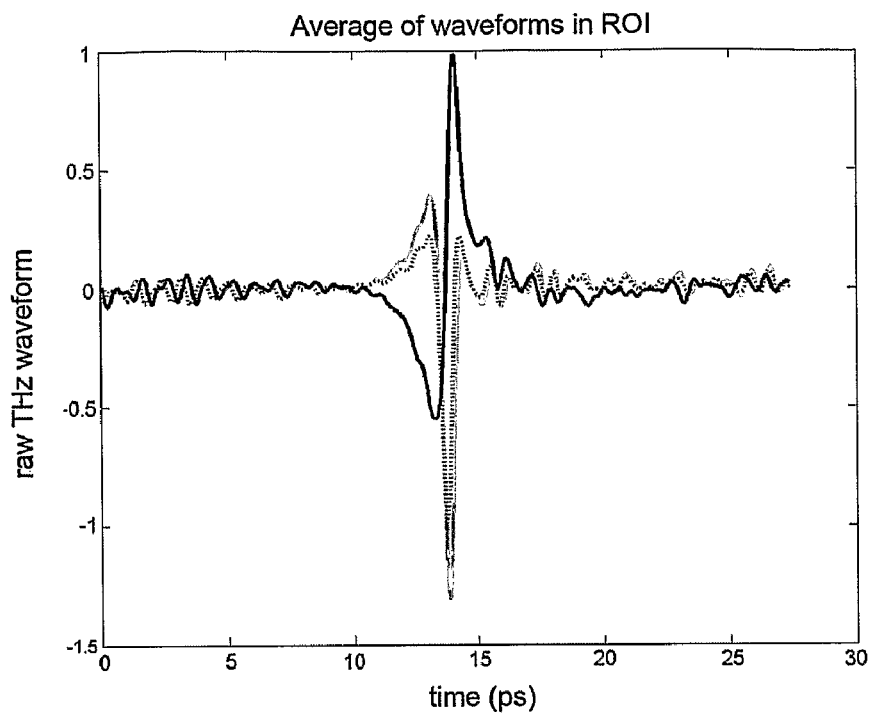
Figure 4B:
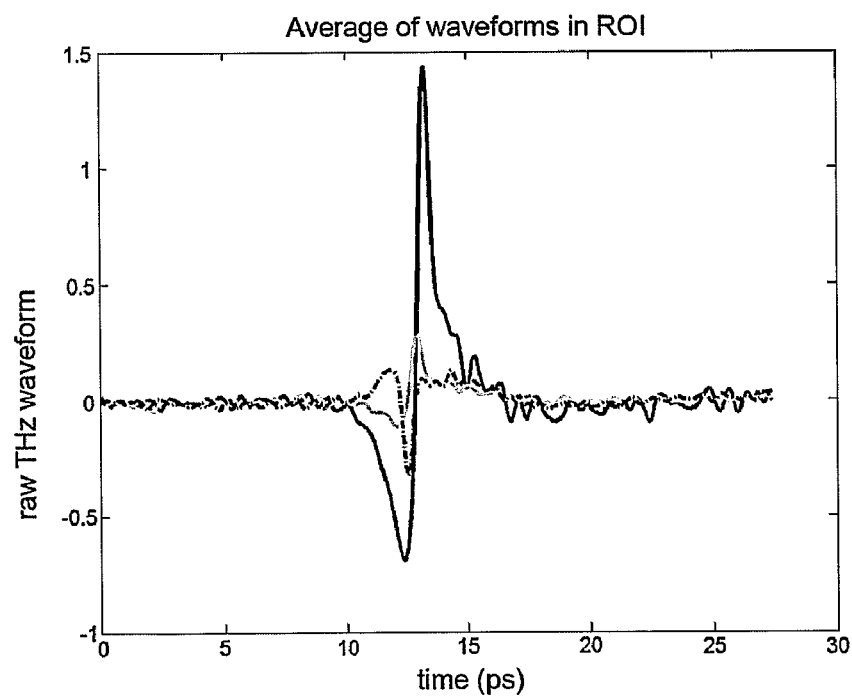
Figure 5A:
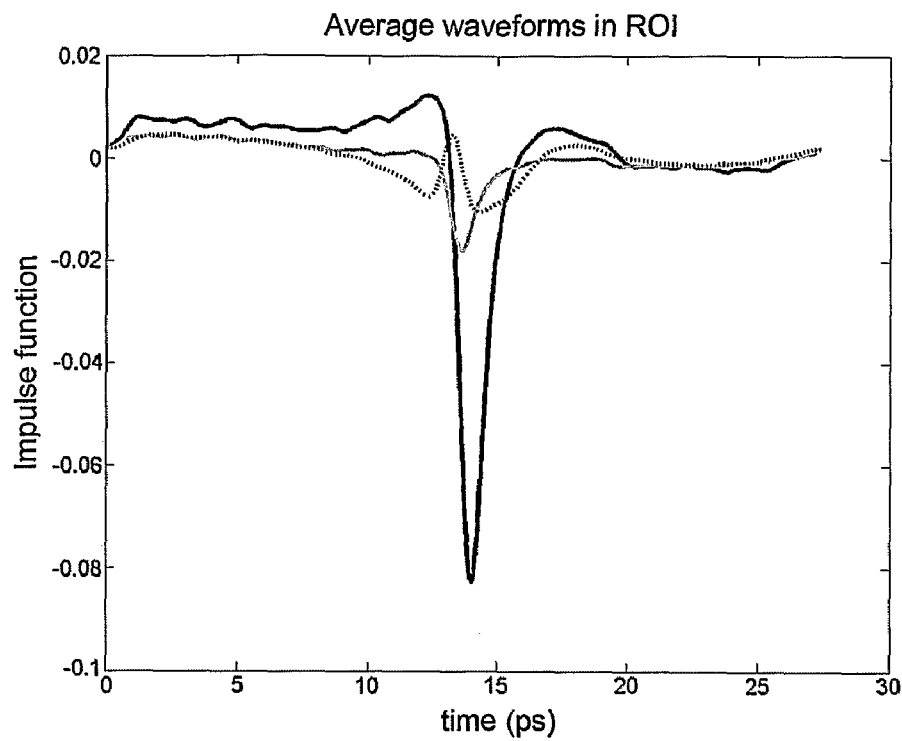
Figure 5B:
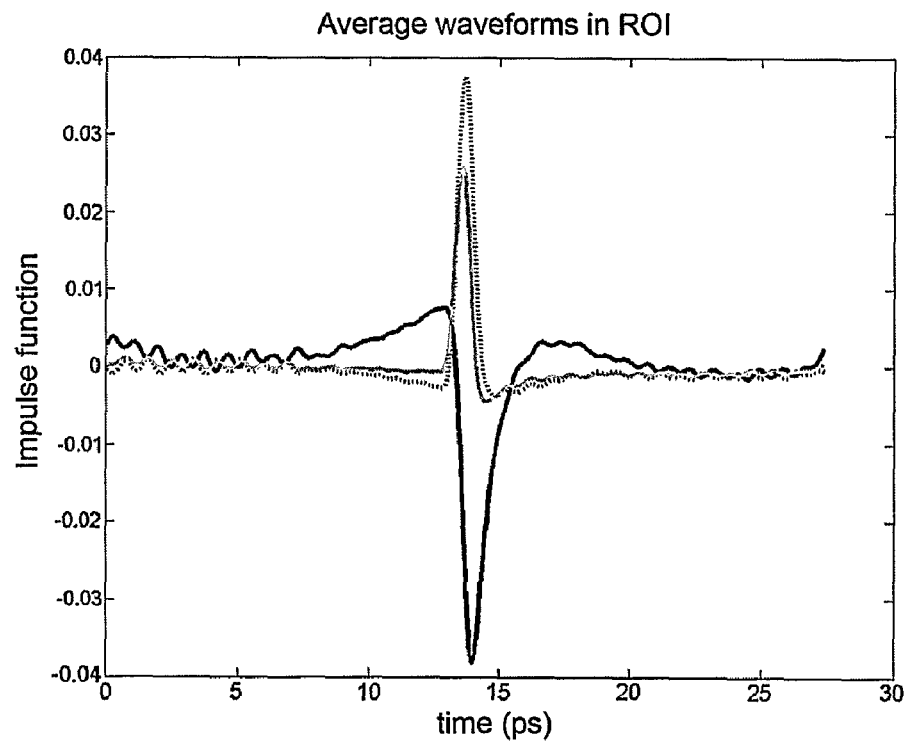
Figure 6A:
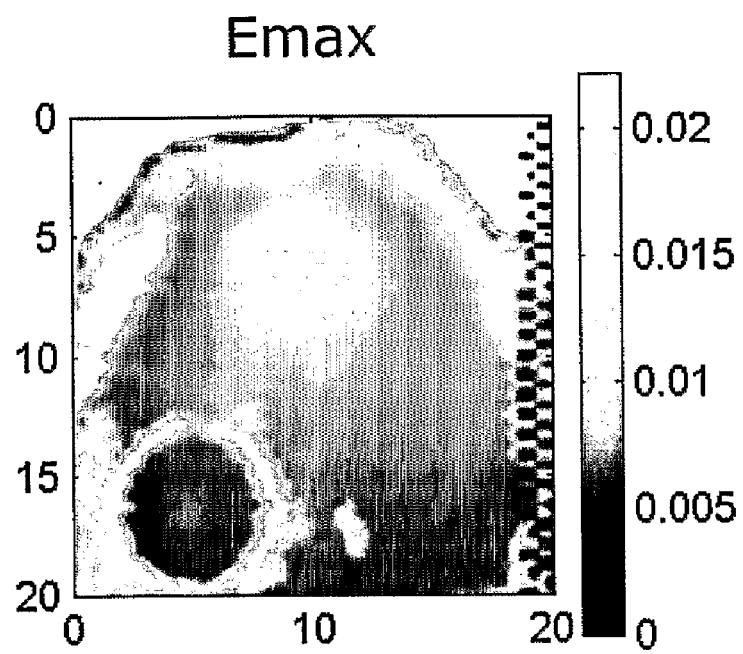
FIG. 6c depicts an image relating to the minimum of the detected impulse function where the window member is constructed of polythene.
FIG. 6d shows the same image as in FIG. 6c but with a quartz window.
FIG. 6e depicts an image relating to the ratio of the impulse function detected maximum to minimum where the window member is constructed of polythene.
FIG. 6f shows the same image as in FIG. 6e but with a quartz window.
Figure 6B:
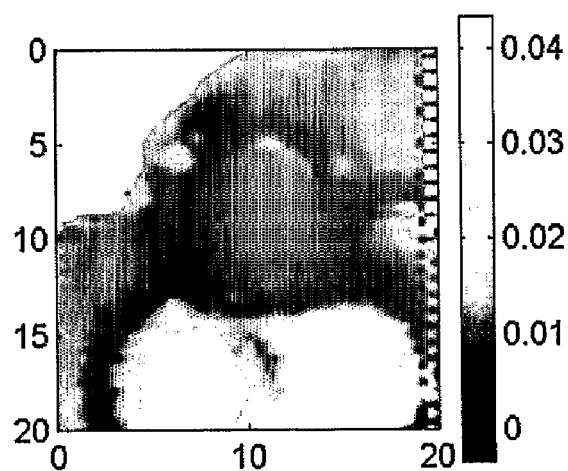
Figure 6C:
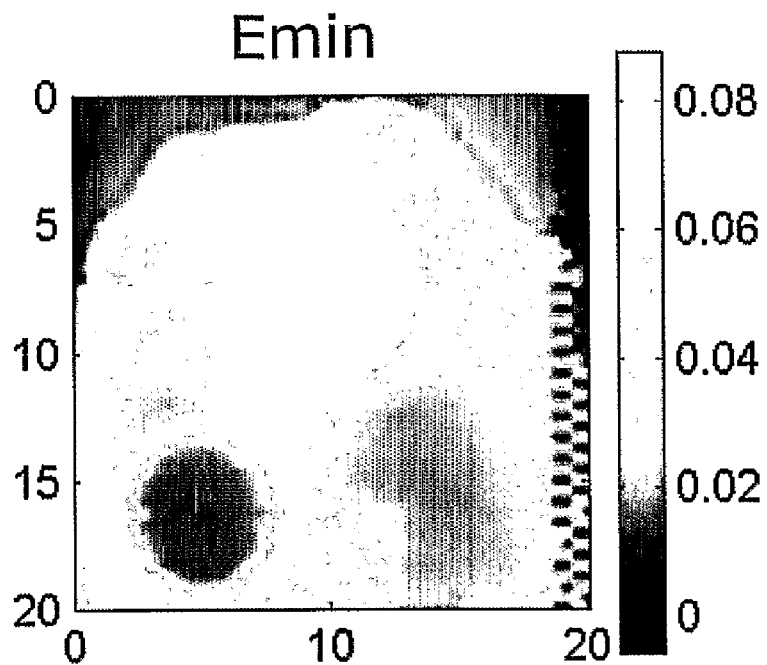
Figure 6D:
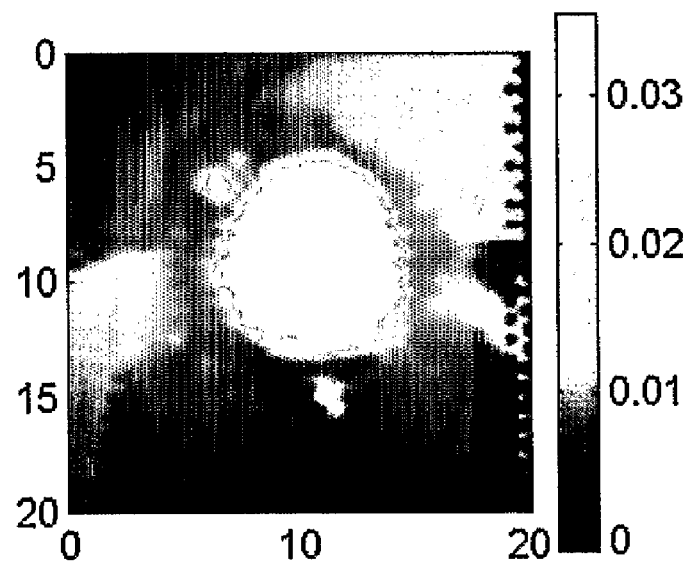
Figure 6E:
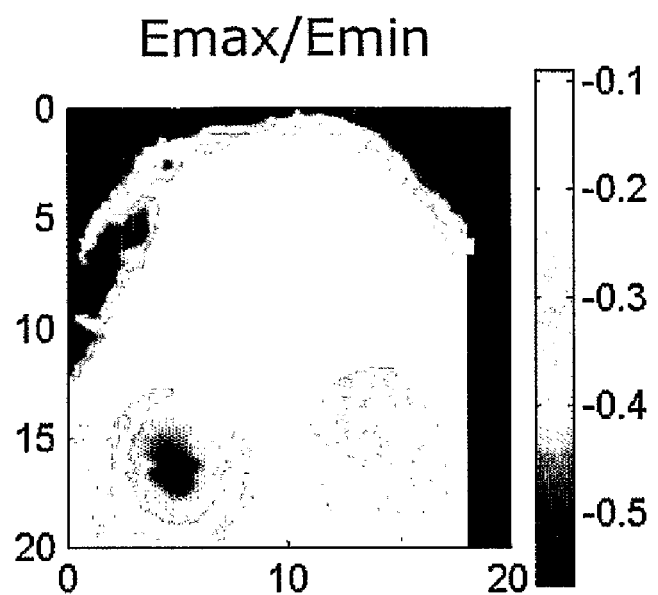
Figure 6F:
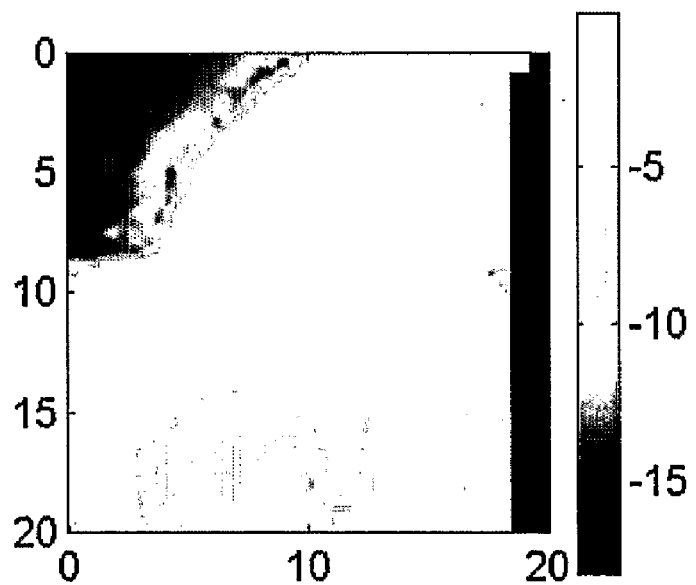
Figure 6G:
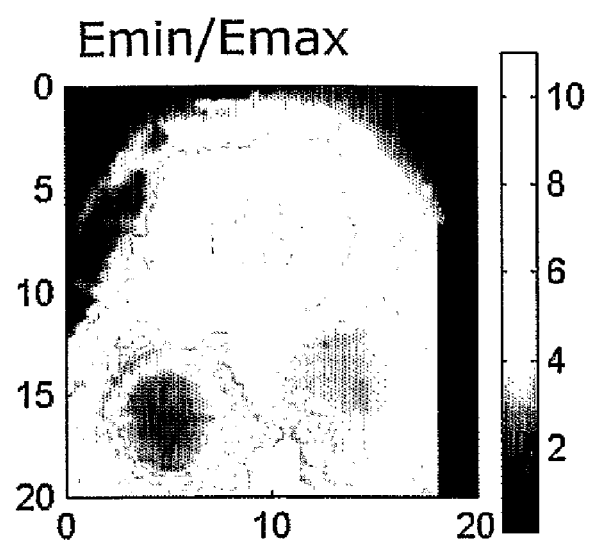
Figure 6H:
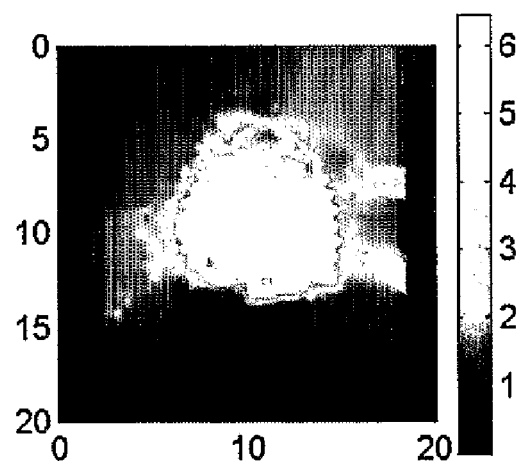

FIG. 6*g* depicts an image relating to the ratio of the impulse function detected minimum to maximum where the window member is constructed of polythene. FIG. 6*h* shows the same image as in FIG. 6*g* but with a quartz window.

The inventors have found that the method of the present invention has produced surprisingly good results for identifying the extent of tumours.

Figure 7:
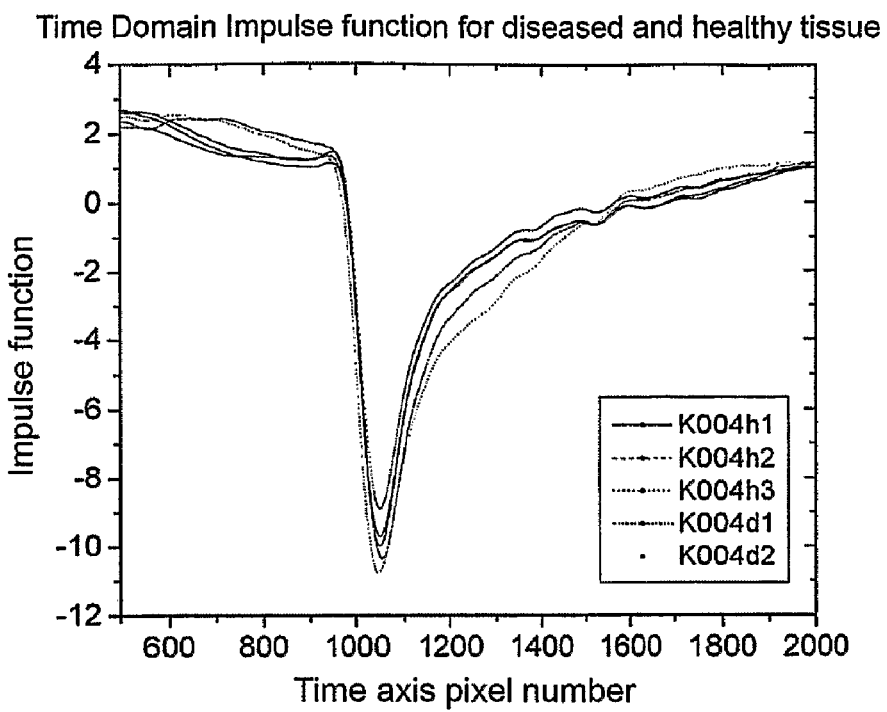

FIG. 7 illustrates a time domain impulse function for diseased and healthy skin tissue as imaged by a prior art system. FIG. 7 shows the impulsed function along the y axis plotted against time delay (arbitrary units) along the x axis. Five traces are shown in FIG. 7 for five different pixels.

From spectroscopy measurements it can be seen that normal adipose tissue has a refractive index in the region of 1.5 whereas skin breast tissue has a refractive index in the region of 2.2 or higher.

Figure 8:
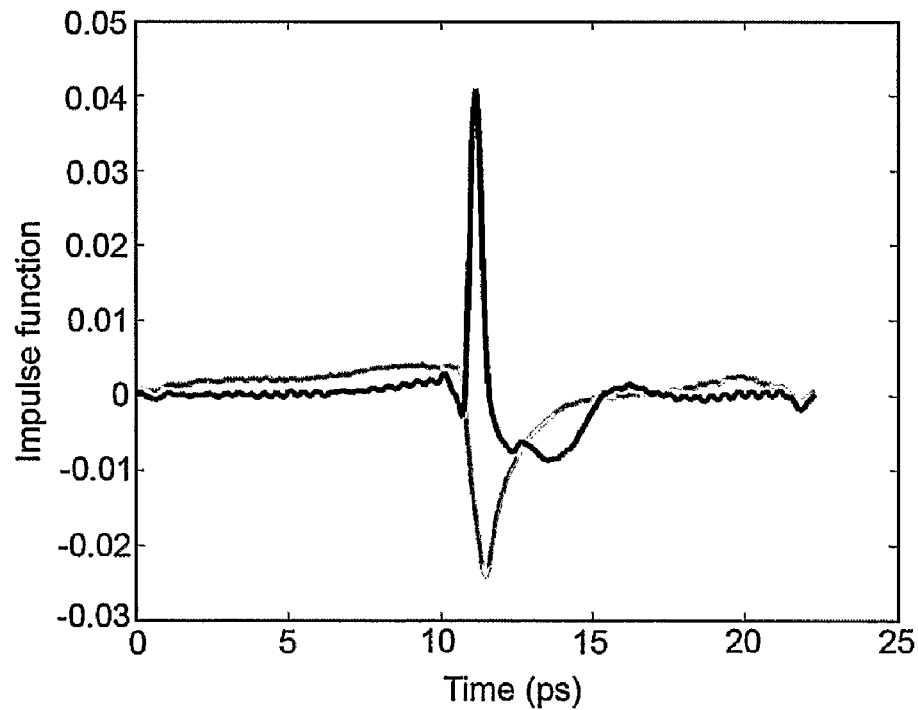

FIG. 8 illustrates a time domain impulse function for diseased and healthy breast tissue obtained by a method according to the present invention. FIG. 8 shows the impulsed function along the y axis plotted against time delay (arbitrary units) along the x axis.

In this example quartz was chosen as the window member since its refractive index (=2.1) is between that of normal and cancerous tissue and also is a close match to the refractive index of skin breast tissue. It can be seen from FIG. 8 that the impulse function relating to the cancerous tissue, which has a higher refractive index than the window member, exhibits a phase change relative to the normal tissue. It is therefore possible to distinguish healthy tissue and diseased tissue by this method.

Figure 9:

FIG. 9 illustrates a visual image of a breast tumour. Diseased tissue 53 shows up as dark areas while normal tissue 55 is white or clear. The boxed area 57 represents the area that was imaged using a THz imaging method according to the present invention.

Figures 10A, 10B:
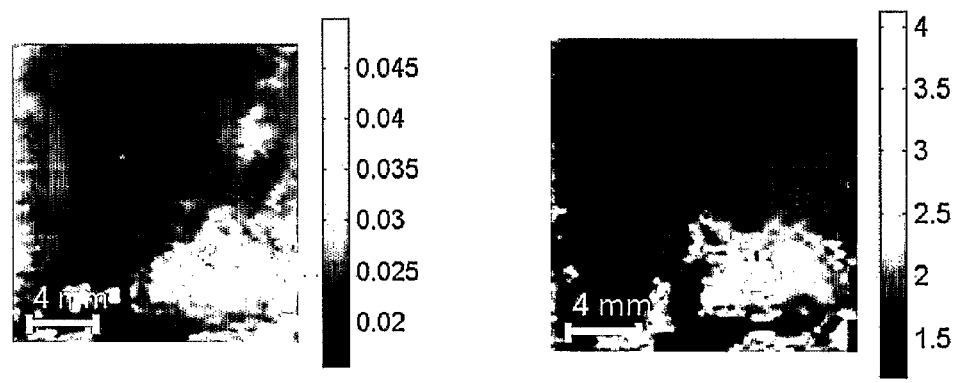

FIG. 10*a* shows the boxed area of FIG. 9 using the parameter Emin. This shows a strong contrast between normal and diseased tissue. FIG. 10*b* shows a similar image using the ratio of Emax to Emin and illustrates the same basic contrast features of FIG. 10*a*.

The invention claimed is:

1. A method of investigating a sample, the sample comprising at least a first material in order to determine the presence of at least one further material, the method comprising the steps of:
    a) irradiating the sample with electromagnetic radiation in the range from 25 GHz to 100 THz;
    b) detecting radiation reflected from the sample;
    c) determining a parameter related to the amplitude of the radiation, which is reflected from the sample, in the time domain;
    d) analysing the parameter derived in step (c) in order to determine if there has been a 180° change in phase of the reflected radiation relative to the radiation irradiating the sample in order to determine if the sample further comprises the at least one further material;
    wherein the irradiating and reflected radiation passes through a window member having a refractive index that falls between the refractive indices of the at least first and at least one further materials such that the irradiating radiation undergoes no change in chase upon being reflected at an interface between the window member and the at least a first material and undergoes a 180° change in phase upon being reflected at an interface with between the window member and the at least one further material.

2. A method of imaging a samples the sample, comprising at least a first material and at least one further material, the method comprising the steps of:
    a) irradiating the sample with electromagnetic radiation in the range from 25 GHz to 100 THz;
    b) detecting radiation reflected from the sample;
    c) determining a parameter related to the amplitude of the radiation, which is reflected from the sample, in the time domain;
    d) generating an image by plotting the value of the parameter calculated in step (c) for different points of the sample to show if there has been a 180° change in phase of the reflected radiation relative to the radiation irradiating the sample,
    wherein the irradiating and reflected radiation passes through a window member having a refractive index that falls between the refractive indices of the at least a first and at least one further materials such that the irradiating radiation undergoes no change in phase upon being reflected at an interface between the window member and the at least a first material and undergoes a 180° change in phase upon being reflected at an interface between the window member and the at least one further material.

3. A method as claimed in claims 1 or 2 wherein the parameter determined in step (c) coincides with a maxima or minima in the detected radiation.

4. A method as claimed in claims 1 or 2 wherein the parameter determined in step (c) corresponds to a ratio of the detected radiation calculated at two separate time values.

5. A method as claimed in claim 4 wherein the ratio is of a maxima to a minima in the detected radiation.

6. A method as claimed in claims 1 or 2 wherein the window member is constructed from one of the following materials: high resistivity silicon, z-cut quartz, TPX, polystyrene or polythene.

7. A method as claimed in claims 1 or 2 wherein the window member has a refractive index which substantially does not vary with frequency.

8. A method of investigating a sample as claimed in claim 1 wherein the at least a first material is normal breast tissue and the at least one further material is cancerous tissue.

9. A method as claimed in claims 1 or 2 wherein the method further comprises the step of:
    obtaining a baseline signal by irradiating the member in the absence of the sample and
    detecting the amplitude of the reflected radiation, and
    wherein in step (c):
    the first parameter is determined by subtracting the baseline signal from the detected amplitude of the radiation reflected from both the member and the sample.

10. An apparatus for imaging a sample comprising at least a first material and at least one further material, the apparatus comprising
    a source for irradiating a sample with a pulse of electromagnetic radiation, said pulse having a plurality of frequencies in the range 25 GHz to 100 Thz;
    detector means for detecting the amplitude of radiation reflected from the sample;
    calculating means for determining a parameter related to the amplitude of the radiation, which is reflected from the sample, in the time domain and configured to determine if there has been a 180° change in phase of the reflected radiation relative to the radiation irradiating the sample;

imaging means for generating an image by plotting the value calculated by the calculating means for different points of the sample;

wherein the apparatus further comprises a window member through which the irradiating and reflected radiation passes, the window member arranged to have a refractive index that falls between the refractive indices of the at least a first and at least one further material of the sample to be imaged such that the irradiating radiation undergoes no change in phase upon being reflected at an interface between the window member and the at least a first material and undergoes a 180° change in phase upon being reflected at an interface between the window member and the at least one further material.

11. The use of quartz in a THz medical scanning apparatus wherein the apparatus comprises a source for irradiating a sample with a pulse of electromagnetic radiation, said pulse having a plurality of frequencies in the range 25 GHz to 100 Thz;

detector means for detecting the amplitude of radiation reflected from the sample;

a quartz window member; and calculating means for determining a parameter related to the amplitude of the radiation, which is reflected from the sample, in the time domain and configured to determine if there has been a 180° change in phase of the reflected radiation relative to the radiation irradiating the sample, wherein the irradiating and reflected radiation passes through the quartz window member such that the irradiating radiation undergoes no change in phase upon being reflected at an interface between the quartz window member and at least a first material of the sample and undergoes a 180° change in phase upon being reflected at an interface between the quartz window member and at least one further material of the sample.

* * * * *